United States Patent [19]

Westernacher et al.

[11] Patent Number: 4,967,019
[45] Date of Patent: * Oct. 30, 1990

[54] METHOD OF MANUFACTURING 2-PROPYN-1-OL

[75] Inventors: Helmut Westernacher, Haltern; Karl Aertken, Duelmen; Thomas Stieren, Haltern, all of Fed. Rep. of Germany

[73] Assignee: Gaf-Huels Chemie GMBH, Marl, Fed. Rep. of Germany

[*] Notice: The portion of the term of this patent subsequent to Aug. 8, 2006 has been disclaimed.

[21] Appl. No.: 354,877

[22] Filed: May 22, 1989

Related U.S. Application Data

[63] Continuation of Ser. No. 166,475, Mar. 10, 1988, Pat. No. 4,855,516.

[30] Foreign Application Priority Data

May 23, 1987 [DE] Fed. Rep. of Germany ....... 3717471
May 23, 1987 [DE] Fed. Rep. of Germany ....... 3717470
May 23, 1987 [DE] Fed. Rep. of Germany ....... 3717468

[51] Int. Cl.$^5$ ................... C07C 27/00; C07C 29/00; C07C 33/042; C07C 45/51
[52] U.S. Cl. .................................. 568/873; 568/486
[58] Field of Search ............... 568/873, 874, 903, 486

[56] References Cited

U.S. PATENT DOCUMENTS 2,421,554  6/1947  Finch et al. .................. 568/486
4,855,516  8/1989  Westernacher et al. ........ 568/873

*Primary Examiner*—J. E. Evans
*Attorney, Agent, or Firm*—Oblon, Spivak, McClelland, Maier & Neustadt

[57] ABSTRACT

A method of manufacturing 2-propyn-1-ol by decomposing 2-butyn-1,4-diol in the presence of a copper acetylide catalyst. 2-propyn-1-ol is produced at high conversion, yield, and purity.

3 Claims, No Drawings

METHOD OF MANUFACTURING 2-PROPYN-1-OL

This is a continuation of application Ser. No. 166,475, filed on Mar. 10, 1988, now U.S. Pat. No. 4,855,516.

BACKGROUND OF THE INVENTION

1. Field of the Invention:

The invention relates to the manufacture of 2-propyn-1-ol (propargyl alcohol, $HC\equiv CCH_2OH$) by catalytic decomposition of 2-butyn-1,4-diol.

2. Discussion of the Background:

2-Propyn-1-ol is used for synthesis of polyenes and other natural substances, and is also employed as a corrosion protection agent in electroplating. In the manufacture of 2-butyn-1,4-diol from formaldehyde and acetylene, 2-propyn-1-ol occurs as a minor byproduct.

In the known methods for manufacturing 2-propyn-1-ol, the starting materials are also formaldehyde and acetylene. The secondary reaction of 2-propyn-1-ol with formaldehyde to form 2-butyn-1,4-diol is suppressed by special reaction conditions.

In Ger. Pat. No. 11 74 765, addition of N-methylpyrrolidone to the reaction mixture is claimed. N-methylpyrrolidone is a good solvent for acetylene, thereby enabling a high acetylene concentration. The reaction of acetylene and formaldehyde in the presence of copper acetylide under the conditions stated leads principally to 2-propyn-1-ol. However, a substantial amount of 2-butyn-1,4-diol is formed. The cost of isolating pure 2-propyn-1-ol from the reaction mixture is high.

According to Ger. Pat No. 1,284,964, acetylene and formaldehyde can be reacted in a solvent, e.g. butyrolactone, with the aid of copper acetylide on a support, to form 2-butyn-1,4-diol and 2-propyn-1-ol. The two products are formed in comparable amounts. High acetylene pressures are used, which necessitates major expenditures on safety, particularly when large scale apparatus is employed.

SUMMARY OF THE INVENTION

One object of the present invention is to provide a method of manufacturing 2-propyn-1-ol at minimal technical cost in funds and resources, and in improved yield and purity.

This and other objects of the invention which will become apparent from the following specification have been achieved by the present process in which 2-butyn-1,4-diol is decomposed at elevated temperature with the aid of a copper acetylide catalyst, to form 2-propyn-1-ol and formaldehyde, and 2-propyn-1-ol is withdrawn from the reaction mixture.

In a preferred embodiment, 2-butyn-1,4-diol is decomposed at elevated temperature in a high-boiling organic solvent with the aid of a copper acetylide catalyst, to form 2-propyn-1-ol and formaldehyde, and 2-propyn-1-ol is separated out by distillation.

DETAILED DESCRIPTION OF THE PREFERRED EMBODIMENTS

For the reaction according to the invention, anhydrous 2-butyn-1,4-diol is preferably used. If the starting material contains water, the water removed must be prior to carrying out the reaction. This may be accomplished, e.g., by heating at reduced pressure.

The favorable temperature range for this reaction is 130°–180° C., preferably 140°–170° C. At insufficient temperature the reaction rate is too low for an industrial process. At excessively high temperature, side reactions and resin formation are marked, with lower yields of 2-propyn-1-ol.

Suitable solvents for the reaction have normal boiling points in the range 130°–240° C. Examples include ethylene glycol, hexanol, octanol, and N-methylpyrrolidone. Ethylene glycol is preferred.

If the reaction is carried out with the solvent boiling under reflux, the distillative isolation of the 2-propyn-1-ol product is facilitated. The reaction may be carried out at normal pressure. To establish a desired boiling temperature, however, a slight vacuum up to 300 mbar vacuum may be applied.

The solution employed contains 2-butyn-1,4-diol in the amount of 20–80 wt. %, Preferably 25–50 wt. %. At concentrations below 20 wt. %, the solvent content is uneconomically high. At concentrations above 80 wt. %, the solution is highly viscous and difficult to handle, and the risk of resin formation is increased.

In this embodiment, the inventive method may be carried out continuously or discontinuously. Thus, the reaction may be carried out in an apparatus comprised of a reaction vessel and reflux condenser, with the solvent boiling under reflux. The 2-propyn-1-ol is enriched at the top of the column, and may be drawn off continuously there. At the same time, losses of starting material may be continuously replaced by dropwise addition of molten 2-butyn-1,4-diol or an aqueous solution of 2-butyn-1,4-diol. The purity of the 2-propyn-1-ol product depends on the reflux ratio selected, and on the separation capability of the column.

According to a second preferred embodiment, 2-butyn-1,4-diol is decomposed at elevated temperature in the presence of a copper acetylide catalyst, to form 2-propyn-1-ol and formaldehyde, and 2-propyn-1-ol is removed from the reaction mixture with the aid of a stripping agent at a pressure of 10–200 mbar.

In general, anhydrous 2-butyn-1,4-diol is used for the reaction according to this embodiment. If a water-containing stripping agent is used, water-containing 2-butyn-1,4-diol may also be used.

The favorable temperature range for this reaction is 120°–170° C., Preferably 130°–155° C. At insufficient temperature the reaction rate is too low for an industrial process. At excessively high temperature, side reactions and resin formation are marked, with lower yields of 2-propyn-1-ol.

2-Propyn-1-ol is removed from the reaction mixture with the aid of a stripping agent introduced to the liquid at reduced pressure. Suitable stripping agents include, e.g., pentanol, butanol, propanol, ethanol, and water. Preferably n-butanol or water is used.

The pressure employed is generally 10–200 mbar, preferably 30–100 mbar.

The mixture of 2-propyn-1-ol and stripping agent which is removed is condensed by cooling, whereupon 2-propyn-1-ol is separated from the stripping agent by fractional distillation or other customary methods.

This embodiment of the inventive method may also be carried out continuously or discontinuously. Losses of 2-butyn-1,4-diol due to conversion can be compensated by addition of additional 2-butyn-1,4-diol along with the stripping agent.

Still another preferred embodiment consists of decomposing 2-butyn-1,4-diol at elevated temperature and pressure in a low-boiling solvent with the aid of a copper acetylide catalyst in the presence of acetylene, to yield 2-propyn-1-ol and formaldehyde, with distillative isolation of 2-propyn-1-ol.

Anhydrous 2-butyn-1,4-diol may be used for the reaction according to this preferred embodiment. If the starting substance contains water, the water must be removed prior to carrying out the reaction. This may be accomplished, e.g., by heating at reduced pressure.

The favorable temperature range for this reaction is 130°–170° C., preferably 140°–160° C. At insufficient temperature the reaction rate is too low for an industrial process. At excessively high temperature, side reactions and resin formation are marked, with lower yields of 2-propyn-1-ol.

Suitable solvents for the reaction have normal boiling points within the range 80°–129° C. Examples include n-butanol, isobutanol, propanol, and pentanol. The preferred solvent is n-butanol.

If the reaction is carried out in a solvent boiling under reflux, the distillative isolation of the 2-propyn-1-ol product is facilitated. As a rule, a mixture of 2-propyn-1-ol and solvent is first obtained; 2-propyn-1-ol may be recovered from this mixture by fractional distillation.

An overall pressure of 1.05–5 bar, preferably 1.05–2 bar, is maintained during the reaction. Acetylene is introduced into the reaction solution under these conditions. Preferably the rate of acetylene feed is 1 to 100 liter per hr per liter solution.

The solution employed contains 2-butyn-1,4-diol in the amount of 20–90 wt. %, preferably 50–70 wt. %.

Concentrations below 20 wt. %, the solvent content is uneconomically high. At concentrations above 90 wt. %, the solution is highly viscous and difficult to handle, and the risk of resin formation is increased.

This embodiment of the inventive method may be carried out continuously or discontinuously. Thus, the reaction may be carried out in an apparatus comprised of a reaction vessel and reflux condenser, with the solvent boiling under reflux. Enriched 2-propyn-1-ol or a mixture of 2-propyn-1-ol and solvent may be continuously withdrawn at the top of the column. At the same time, the losses of starting materials may be made up continuously by dropwise addition of 2-butyn-1,4-diol and solvent. The purity of the 2-propyn-1-ol product depends on the boiling point difference, the reflux ratio selected, and the separation capability of the column.

The copper acetylide catalyst suitable for the inventive method contains copper acetylide and a support, e.g. magnesium silicate, and may further contain bismuth oxide, among other substances. The catalyst generally comprises Cu in the amount of 10–50 wt. %, preferably 20–35 wt. %. The preparation of such catalysts is described in Ger. Pat. No. 2,719,745.

The copper acetylide catalyst is employed in an amount of 2–20 wt. % based on the weight of the reaction solution. Preferably the copper acetylide catalyst is present in the amount of 5–15 wt. %.

For copper acetylide present at <2 wt. %, the reaction rate is too low; for >20 wt. %, the increase in reaction rate is insignificant; hence higher catalyst concentrations are uneconomical.

The method has the advantage that it can be carried out in simple apparatus, and that 2-propyn-1-ol is produced at high conversion, yield, and purity.

Other features of the invention will become apparent in the course of the following descriptions of exemplary embodiments which are given for illustration of the invention and are not intended to be limiting thereof.

EXAMPLES

Example 1

The copper acetylide catalyst required was prepared according to Ger. Pat. No. 2,719,745, and was water-washed and dried before use. It comprised Cu in the amount of 35 wt. %, $Bi_2O_3$ in the amount of 3 wt. %, and magnesium silicate in the amount of 43 wt. %.

In a 1 liter glass flask with stirrer, dropping funnel, and packed column equivalent to 10 theoretical plates, 500 g ethylene glycol, 130 g 2-butyn-1,4-diol, and 45 g copper acetylide catalyst were brought to boiling at 162° C., under stirring and at reduced pressure, specifically about 460 mbar. 2-propyn-1-ol formed and was enriched at the top of the column and was drawn off there continuously, with a reflux ratio of 5:1. In 4 hr, 55 g 2-butyn-1,4-diol was converted, which was replaced by adding molten 2-butyn-1,4-diol dropwise.

Yield: 34 g 2-propyn-1-ol (94% of theoretical). Purity (by GC): >99%.

Example 2

The same copper acetylide catalyst as in Example 1 was employed.

In a 2 liter reaction vessel with dropping funnel and stirrer, 1,957 g 2-butyn-1,4-diol and 60 g catalyst were charged. In 1 hr, the residual water was driven off at 40°–50° C. and about 25 mbar, leaving water in the amount of <0.1 wt. %.

Then the mixture was heated to 150° C., at about 25 mbar, whereupon the formation of 2-propyn-1-ol began to take place. Then, 150 ml/hr n-butanol was added from the dropping funnel directly into the liquid phase, as a stripping agent. The off-gases from the reaction vessel were condense into a receiver at −10° C.

Over a test period of 66 hr, 1,590 g 2-butyn-1,4-diol was converted, and 776 g 2-propyn-1-ol was formed, for a yield of 75% of theoretical.

Example 3

The same copper acetylide catalyst as in Example 1 was employed.

In a 2.1 liter distillation vessel with magnetic stirrer, feed tube, and packed column equivalent to about 7 theoretical plates, 30 g copper acetylide catalyst was suspended in 1,000 g 2-butyn-1,4-diol and 500 g n-butanol. Acetylene was then passed at 10 liter/hr through the liquid. After this gas stream was begun, the mixture was heated to boiling at 140°–142° C. A pressure of 1.08–1.09 bar was measured at the top of the column.

The distillate comprised of n-butanol and 2-propyn-1-ol was withdrawn at the top of the column at a rate of 70–80 ml/hr, at a reflux ratio of 10:1. The losses through distillation were made up by addition of 2-butyn-1,4-diol and n-butanol to the reaction mixture in the bottom of the still.

After 25 hr, 170 g 2-butyn-1,4-diol had been converted, with production of 94 g 2-propyn-1-ol, for a yield of 85% of theoretical.

Pure 2-propyn-1-ol was obtained from the solution by fractional distillation.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of manufacturing 2-propyn-1-ol, comprising the steps of:
    decomposing 2-butyn-1,4-diol at elevated temperature in the presence of a copper acetylide catalyst, to form a reaction mixture comprising 2-propyn-1-ol and formaldehyde, and
    removing said 2-propyn-1-ol from said reaction mixture,
    wherein said 2-butyn-1,4-diol is decomposed at elevated temperature and pressure above 1 bar, in a low-boiling organic solvent in the presence of a copper acetylide catalyst in the presence of acetylene, to form a reaction mixture comprising 2-propyn-1-ol and formaldehyde, and said 2-propyn-1-ol is removed by distillation.

2. The method of claim 1, wherein said decomposing step is carried out in solvents with boiling points in the range of 80° to 129° C.

3. The method of claim 1, wherein acetylene is introduced into the solvent during said decomposing step, and an overall pressure of 1.05 to 5 bar is maintained.

* * * * *